United States Patent [19]

Hietala et al.

[11] Patent Number: 5,296,437
[45] Date of Patent: Mar. 22, 1994

[54] CATALYST FOR METATHESIS REACTIONS OF OLEFINES AND A METHOD FOR PREPARING IT AS WELL AS THE METATHESIS REACTION CONCERNED

[75] Inventors: Jukka Hietala; Pekka Knuuttila, both of Porvoo; Markku Leskelä, Espoo; Reijo Sillanpää, Kaarina; Ari Lehtonen, Turku, all of Finland

[73] Assignee: Neste OY, Finland

[21] Appl. No.: 915,098

[22] Filed: Jul. 16, 1992

[30] Foreign Application Priority Data

Jul. 30, 1991 [FI] Finland .................................. 913627

[51] Int. Cl.$^5$ .............................................. B01J 23/30
[52] U.S. Cl. .................................... 502/305; 502/150; 502/172; 585/643; 585/671; 556/57; 556/58
[58] Field of Search ............... 502/227, 242, 349, 350, 502/150, 152, 156, 172, 305; 556/57, 58; 585/643, 671

[56] References Cited

U.S. PATENT DOCUMENTS

| | | | |
|---|---|---|---|
| 3,450,797 | 6/1969 | Schafer et al. | 502/152 |
| 3,956,178 | 5/1976 | Greco et al. | 252/429 B |
| 4,550,216 | 10/1985 | Basset et al. | 585/645 |
| 4,559,320 | 12/1985 | Reusser | 502/251 |
| 4,818,442 | 4/1989 | Vanderveen et al. | 260/405.5 |

FOREIGN PATENT DOCUMENTS 0056013 7/1982 European Pat. Off.
0129474 12/1984 European Pat. Off.
0152112 8/1985 European Pat. Off.

Primary Examiner—Asok Pal
Assistant Examiner—P. Achutamurthy
Attorney, Agent, or Firm—Steinberg & Raskin

[57] ABSTRACT

The invention relates to a catalyst to be utilized in the metathesis reactions of olefines, the catalyst comprising an after-treated tungsten complex containing diol ligands and hydrocarbon ligands, which are benzenes substituted with a lower alkyl group. The invention also relates to a method for preparing a heterogenous catalyst to be used in the metathesis reaction of olefines as well as to a metathesis process for the conversion of olefines.

17 Claims, No Drawings

CATALYST FOR METATHESIS REACTIONS OF OLEFINES AND A METHOD FOR PREPARING IT AS WELL AS THE METATHESIS REACTION CONCERNED

BACKGROUND OF THE INVENTION

The metathesis, or in other words the disproportionation, of olefines relates to a reaction wherein one or more olefines are converted into olefines having a different molecular weight. An olefine may be disproportionated with itself into an olefine having a higher molecular weight and into an olefine having a lower molecular weight. In this case, the reaction may be called "self-disproportionation". Two different olefines may also be converted into other olefines by means of the metathesis reaction In order to function, the metathesis reactions of olefines require a catalyst system, which includes a transition metal compound, often a cocatalyst and sometimes also a compound acting as a promoter. The catalyst systems based on tungsten or molybdenum are especially efficient. Such catalysts generally comprise a tungsten or molybdenum oxide on an inorganic carrier, which is e.g. silica or alumina. It is known to add different substances as a promoter to such catalyst. Thus, e.g. according to EP publication 152,112, tungsten oxide or other titanium-containing substances are added to the surface of the catalyst as a promoter According to U.S. Pat. No. 4,559,320, it is known to use a tungsten catalyst on a silica carrier, into which magnesium oxide is additionally mixed. According to EP publication 56,013, a catalyst composition is known comprising a molybdenum oxide or a tungsten oxide on a silica carrier.

According to U.S. Pat. No. 3,956,178, a metathesis catalyst of three components is known, which catalyst is prepared from a tungsten compound, an organic ligand and an organo-metallic compound. In this patent, the tungsten compound is a titanium oxychloride and the organic ligand contains a nitrile or ester group. As examples of ligands are mentioned phthalodinitrile, adipo nitrile and ethyl phthalate.

According to U.S. Pat. No. 4,550,216, a metathesis catalyst is known, which comprises a compound of tungsten, a halogen and a phenoxy group, which compound is possibly substituted.

SUMMARY OF THE INVENTION

This invention relates to a catalyst to be used in the metathesis reactions of olefines. The invention also relates to a method of preparing such catalyst.

Still further, the invention relates a metathesis process for the conversion of olefines into olefines having a different molecular weight.

It is a primary object of the present invention to provide totally new metathesis catalyst from organo-tungsten compounds.

It is another object of the invention to provide for the production of the new metathesis catalysts of the present invention.

Still further, it is an object of the present invention to provide for a metathesis process for the conversion of olefines into olefines having a different molecular weight.

With the above and other objects in view, the new metathesis catalysts of the present invention are mainly characterized in that the same comprise an after-treated tungsten complex which contains diol ligands and hydrocarbon ligands, which are benzenes substituted with a lower alkyl group. The process of after-treating is the process of impregnating a catalyst in a carrier and then calcinating the catalsyt.

The inventive method for preparing a catalyst is characterized that a) a complex between an inorganic tungsten salt and a diol is formed, b) the complex obtained is caused to react with a benzyl anion or a benzyl anion substituted with a lower alkyl group for obtaining a tungsten complex containing diol ligands, benzyl ligands or benzyls ligands substituted with a lower alkyl group, and c) the tungsten complex obtained is impregnated into a carrier and calcinated.

The inventive metathesis process for the conversion of olefines, wherein the catalyst comprising a tungsten compound converts the olefine into olefines having a different molecular weight, is characterized in that the heterogenous catalyst comprises an after-treated tungsten complex, which contains diol ligands and unsubstituted benzyl ligands or benzyl ligands substituted with a lower alkyl group.

The tungsten complexes, in which a diol or a benzene substituted with a lower alkyl group, e.g. mesitylene, are used as ligands may be converted into heterogenous catalysts, which function in the metathesis of olefines at a higher activity than conventional catalysts, in which ammonium tungstenate acts as a precursor. In addition, the preparation of the catalysts is easier, since the quantity of metal is low and the solubility in polar organic solvents is good.

The fact that the structures of the inventive synthesized precursors are of a novel type, is based on spectra and the determination of the released HCl. Thus, the inventive catalyst is used in the metathesis reaction, in which C=C bonds decompose and the moieties combine again. For example propene may be prepared from ethylene and 2-butene.

The inventive catalyst is prepared from a tungsten complex, in which as ligands are used diols and benzenes substituted with a lower alkyl group.

In the first step, an inorganic tungsten salt and a diol form a complex according to the equation (1):

$$WCl_6 + 2\ diolH_2 \rightarrow WCl_2(diol)_2 + 4HCl \qquad (1)$$

in which $diolH_2$ = a diol compound, preferably a picanol or trans-1,2-cyclohexane diol.

Thereafter, the tungsten oxide obtained reacts with a bromide of a benzene substituted with a lower alkyl group, in this example with a mesitylene bromide, and a metallic magnesium for obtaining a catalyst precursor in accordance with the equation (2):

$$WCl_2(diol)_2 + 2ArCH_2Br + 2\ Mg \rightarrow W(ArCH_2)_2(diol)_2 + MgBr_2 + MgCl_2 \qquad (2)$$

in which $ArCH_2$ is a mesitylene ligand.

DESCRIPTION OF PREFERRED EMBODIMENTS

The examples which follow are given to further illustrate the present invention. The scope of the invention is not meant to be limited thereto.

The syntheses were made in a nitrogen atmosphere using a Schlenck technique. The solvents, except for the tetrahydrofurane, were dried by calcium hydride and distilled, and the tetrahydrofurane was dried with a sodium-benzophenon mixture before the distillation. The diols were sublimated before use.

The hydrochloride released in the reactions was determined by bubbling the reaction solution with nitrogen and by passing the solution into an 0.10M NaOH solution, which was titrated.

For the determination of the tungsten content and the chlorine content of the products, the same were decomposed by means of a concentrated nitric acid. The chloride was potentiometrically nitrated and the tungsten was gravimetrically determined as an oxide. As for the catalysts, the tungsten was determined by means of XRF.

The infrared spectra were run in nujol (JASCO IR-810), the NMR spectra were run in carbon tetrachloride or deuterochloroform (JEOL JNM-PMX 60, JEOL GSX-400).

The catalysts were tested in a microreactor in a quartz-glass tube, through which the purified propylene was passed (molecular sieves and copper catalyst). A sample of the gas flow passed through the catalyst was taken automatically at intervals of one hour and a gas chromatogram (column Chrompackin Fused Silica) was run.

EXAMPLES 1-3

A reaction of tungsten hexachloride with trans-1,2-cyclohexane diol

EXAMPLE 1

A reaction of tungsten hexachloride and trans-1,2-cyclohexane diol in a substance quantity ratio 1:1

$WCl_6 + chdH_2 \rightarrow WCl_4(chd) + 2\ HCl$ 1.635 g (4.12 mmol) of tungsten hexachloride was dissolved in a Schlenk tube, in 15.0 ml of carbon tetrachloride. 0.4214 g (3.63 mmol) of trans-1,2-cyclohexane diol was added to the solution. The solution was admixed with a magnet mixer, and it was allowed to reflux for one hour. Thereafter, acid formation was no longer observed. The liquid phase was evaporated under an underpressure, i.e., sub-atmospheric pressure. The product was a black solid substance, which dissolved in 1,2-dimethoxy ethane and methanol. On the basis of an IR-spectrum, there was no organic moiety in the product. The test was repeated by using hexane as a solvent, whereby the product was similar to that obtained above.

EXAMPLE 2

A reaction of tungsten hexachloride and trans-1,2-cyclohexane diol in a substance quantity ratio 1:2

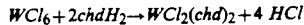

$WCl_6 + 2chdH_2 \rightarrow WCl_2(chd)_2 + 4\ HCl$ 1.276 g (3.22 mmol) of tungsten hexachloride and 0.7474 g (6.44 mmol) of trans-1,2-cyclohexane diol were dissolved in 15.0 ml of carbon tetrachloride. The solution was admixed and it was allowed to reflux for one and a half hours. Thereafter, acid formation was no longer observed. After the evaporation of the liquid phase, a red-brown substance was obtained, which dissolved well in toluene, chloroform, 1,2-dimethoxy ethane and methanol. It dissolved poorly in carbon tetrachloride, and it did not dissolve at all in hexane. From the compound were measured IR and $^1$H NMR spectra (cf. Table 1). On the basis of these, the compound contains cyclohexane diolato groups bound to the tungsten.

69.6 mg of the cyclohexane compound of tungsten prepared was decomposed with 0.5 ml of concentrated nitric acid and 9.5 ml of water was added to the mixture. The released chloride ions were titrated potentiometrically by using a calomel and silver electrode. According to the determination, the compound contained 13.7% of chlorine.

For the determination of the tungsten, 102.2 mg of the compound prepared was admixed into 15.0 ml of concentrated nitric acid and 15.0 ml of water. The mixture was cooked for half an hour, whereafter a pale yellow $WO_3$ was separated by filtration. The tungsten oxide was dried by maintaining it at a temperature of 850° C. for two hours. The oxide was weighed and according to the weight the quantity of tungsten obtained was 42.4%. If it is assumed that the four chloroligands of tungsten hexachloride are replaced with two biserrate cyclohexane diolato ligands, the WCl(chd)$_2$ thus obtained would contain 14.7% of chlorine and 38.1% of tungsten.

EXAMPLE 3

A reaction of tungsten hexachloride and trans-1,2-cyclohexane diol in the cold was effected by dissolving 1.899 g (4.79 mmol) of tungsten hexachloride in 20.0 ml of 1,2-dimethoxyethane and adding 1.112 g (9.59 mmol) of trans-1,2-cyclohexane diol to the solution. The solution was maintained at a temperature of $-15°$ C. and it was admixed by a magnet mixer. After mixing of five hours, no removal of the acid was observed. The solvent was evaporated under an underpressure, i.e., sub-atmospheric pressure. The product was a dark-brown, tough oily substance, which turned blue in connection with the sampling. The dark-blue colour possibly results from the reduction of the tungsten.

EXAMPLES 4 and 5

A reaction of tungsten hexachloride and pinacol

EXAMPLE 4

A reaction of tungsten hexachloride and pinacol in a substance quantity ratio 1:1

$WCl_6 + pinH_2 \rightarrow WCl_4(pin) + 2\ HCl$ 0.807 g (2.04 mmol) of tungsten hexachloride was dissolved in 15.0 ml of carbon tetrachloride. 0.2405 g (2.04 mmol) of pinacol was added to the solution, and it was allowed to reflux for two hours, after which no acid was removed. The liquid phase was evaporated from a green solution when subjected to an underpressure, i.e., sub-atmospheric pressure. The product was a green solid substance, which rapidly turned blue when coming into contact with air. The decomposition was very rapid, due to which IR—and $^1$H NMR-spectra could not be measured from the compound. The green and blue colours relate to reduced tungsten compounds.

EXAMPLE 5

A reaction of tungsten hexachloride and pinacol in substance quantity ratio 1:2

$2WCl_6 + 4pinH_2 \rightarrow [WCl(pin)_2]_2 + 4\ HCl + Cl_2$ 1.600 g (4.04 mmol) of tungsten hexachloride was dissolved in 25.0 ml of carbon tetrachloride and 0.9645 g (8.16 mmol) of pinacol was added to the solution. All of the pinacol did not dissolve in this step. The reaction mixture was mixed with a magnet mixer, and it was allowed to reflux for four hours. After this, no acid formation could be observed. When the reaction advanced, the pale green solution turned dark blue. After the evaporation of the liquid phase, the product obtained was a strongly blue powdery substance. An IR-spectrum was measured from the product (cf. Table 1).

105.9 mg of the compound prepared was decomposed by mixing it in 0.5 ml of concentrated nitric acid. After this, 9.5 ml of water was added to the mixture, and the chloride content was determined. The content obtained was 7.6% (the calculated content was 7.7%).

TABLE 1

Characteristic IR absorptions and 1H NMR spectra of alkoxo compounds of tungsten

| Compound | Absorption peaks of IR spectrum ($cm^{-1}$) | | 1H NMR spectrum ($\delta$/ppm) |
|---|---|---|---|
| $WCl_2(chd)_2$ | 1040 | C—O | 1.2 |
| | 1000 | | 3.6 |
| | 900–600 | W—O | 3.7 |
| $WOCl_2(chd)_2$ | 1040 | C—O | |
| | 1000 | W—O | |
| | 900–600 | W—O | |
| $[WCl(pin_2)]_2$ | 1140 | C—O | |
| | 960–620 | W—O | |
| $WOCl_2(pin)$ | 1140 | C—O | |
| | 980 | W=O | |
| | 960–600 | W—O | |
| $W(chd)_2(mes)_2$ | | | 1.2;1.8 |
| | | | 2.2;2.4 |
| | | | 3.8 |
| | | | 6.9 |
| $W(mes)_2(pin)_2$ | 1160 | C—O | 2.3;2.4 |
| | 960–900 | | 6.9 | chd = cyclohexane diolato ligand
mes = mesitylene ligand
pin = pinacolato ligand

EXAMPLE 6

Preparation of dimesitylene dipinacolato tungsten 0.613 g (1.55 mmol) of tungsten hexachloride was dissolved in 10.0 ml of toluene. 0.994 g (3.10 mmol) of tetrabutyl ammonium nitrate and 3.10 mmol of pinacol, dissolved in 15.0 mol of toluene, were added to the solution The solution was mixed and it was allowed to reflux for six hours. As the reaction advanced, two liquid layers formed in the vessel, the lower one of which layers was an orange and the upper one a yellow solvent. The orange solvent was dissolved in 10.0 ml of tetrahydrofurane, and 3.1 mmol (0.08 g) of magnesium and 3.1 mmol (9.47 ml) of bromine mesitylene were added to the solution. The solution was separated by decantation from a non-reacting magnesium and the salt formed. The solvent was removed from the yellow solution by evaporating the solution under an underpressure, i.e., sub-atmospheric pressure.

A 1H NMR spectrum and an IR spectrum were measured from the brown yellow oily product (Table 1). The compound formed in the reaction contained a mesitylene ligand and a pinacolato ligand bound to the tungsten.

$WCl_6 + 1pinH_2 \rightarrow WCl_2(pin)_2 + 4\ HCl$

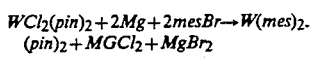

$WCl_2(pin)_2 + 2Mg + 2mesBr \rightarrow W(mes)_2\text{-}(pin)_2 + MGCl_2 + MgBr_2$

PREPARATION AND TESTING OF CATALYSTS

The catalysts were prepared by separately impregnating each precursor (in one catalyst the diol was pinacol and in the other trans-1,2-cyclohexane diol) from THF into silica (PQ Corporation, CS-1231) and by calcinating with nitrogen at 600° C.

The catalysts were tested by passing propene through a catalyst bed at 400° C. A WHSV $4h^{-1}$ conversion was observed in connection with both catalysts to be ca. 50%. (WHSW = weight hourly space velocity, i.e. 1 g of the feeding rate (g) flowing through the quantity of the catalyst per hour.) In the reference catalyst $WO_3$/$SiO_2$, which contained the same quantity of tungsten (2%), the conversion was clearly below 50%. See Tables 2,3 and 4.

EXAMPLE 7

The sample was dimesitylene dipinacolato tungsten. A $^1$C-NMR and a $^1$H-NMR was run from the sample with a 400 MHz device. The spectra may be fitted into the assumed structure.

The sample was known to dissolve in THF, due to which a catalyst impregnated from this solution was prepared, which catalyst contained 0.1294 g of the sample and 0.4450 g of silica. A calcination was performed in a nitrogen flux (ca. 10 l/h, 600° C., 1 h). During the calcination it was observed that a green and brown oil condensed in the reactor tube. It was allowed to react with propene, and test results showing the activity of the metathesis catalyst are shown in Table 2.

TABLE 2

ACTIVITY OF A METATHESIS CATALYST

| | |
|---|---|
| No. of run: | L2 |
| Date: | Feb 12–14, 1990 |
| PRECURSOR: | Dimesitylene dipinacolato tungsten |
| Carrier: | SiO2 PQ cs-1231 0.6–1.6 mm |
| Mass of catalyst (g): | 0.3445 |
| Area of catalyst (m²/g): | 310 |
| Molar mass of metal (g/mol): | 183.85 |
| Content of metal (%): | 2.5 |
| Temperature (°C.): | 400 |
| Activation: | N2 ca. 10 l/h 600° C. 1 h |
| Propylene flow (l/h): | 1–6 |

| Time (h) | Ethylene (%) | Propylene (%) | Trans-2-butene (%) | 1-butene (%) | Cis-2-butene (%) | Others (%) | Butenes (%) | Propylene conversion (%) | Activity (g/gh) | Notes |
|---|---|---|---|---|---|---|---|---|---|---|
| 0.0 | 11.968 | 44.553 | 14.058 | 6.673 | 10.667 | 12.071 | 31.408 | 51.4 | 82.5 | propylene 1.0 l/h |
| 1.0 | 9.008 | 48.017 | 18.137 | 3.918 | 14.128 | 6.792 | 36.183 | 53.1 | 85.2 | |
| 2.0 | 8.632 | 47.618 | 17.600 | 4.371 | 13.646 | 8.133 | 36.617 | 52.9 | 84.9 | |

TABLE 2-continued

ACTIVITY OF A METATHESIS CATALYST

| | | | | | | | | | |
|---|---|---|---|---|---|---|---|---|---|
| 3.0 | 8.855 | 47.136 | 17.239 | 4.603 | 13.403 | 8.764 | 35.245 | 52.9 | 84.9 | |
| 4.0 | 8.307 | 47.424 | 17.282 | 4.663 | 13.401 | 8.923 | 35.346 | 52.8 | 84.8 | |
| 5.0 | 8.361 | 46.489 | 17.337 | 4.634 | 13.427 | 8.752 | 35.398 | 52.8 | 84.8 | |
| 6.0 | 8.195 | 47.515 | 17.344 | 4.556 | 13.440 | 8.902 | 35.340 | 52.7 | 84.7 | |
| 7.0 | 8.089 | 47.620 | 17.374 | 4.530 | 13.485 | 8.902 | 35.389 | 52.7 | 84.6 | |
| 8.0 | 8.769 | 47.548 | 17.402 | 4.346 | 13.503 | 8.432 | 35.251 | 52.7 | 84.6 | |
| 9.0 | 8.625 | 47.670 | 17.434 | 4.371 | 13.559 | 8.341 | 35.364 | 52.7 | 84.6 | |
| 10.0 | 8.341 | 47.402 | 17.375 | 4.504 | 13.482 | 8.896 | 35.361 | 52.8 | 84.8 | |
| 11.0 | 8.519 | 47.363 | 17.391 | 4.408 | 13.496 | 8.823 | 35.295 | 52.8 | 84.8 | |
| 12.0 | 8.484 | 47.609 | 17.524 | 4.407 | 13.575 | 8.401 | 35.506 | 52.8 | 84.8 | |
| 13.0 | 8.352 | 47.728 | 17.626 | 4.215 | 13.740 | 8.339 | 35.581 | 52.8 | 84.8 | |
| 14.0 | 8.391 | 47.816 | 17.711 | 4.198 | 13.738 | 8.146 | 35.647 | 52.8 | 84.8 | |
| 15.0 | 8.331 | 47.781 | 17.748 | 4.224 | 13.789 | 8.127 | 35.761 | 52.9 | 84.9 | |
| 16.0 | 8.387 | 47.874 | 17.828 | 4.179 | 13.897 | 7.835 | 35.904 | 52.9 | 85.0 | |
| 17.0 | 8.413 | 47.778 | 17.747 | 4.152 | 13.774 | 8.136 | 35.673 | 52.8 | 84.8 | |
| 18.0 | 8.225 | 50.010 | 19.921 | 2.266 | 15.728 | 3.850 | 37.915 | 53.2 | 172.6 | propylene 2.0 l/h |
| 19.0 | 8.332 | 50.285 | 20.038 | 2.199 | 15.803 | 3.343 | 38.040 | 53.2 | 172.4 | |
| 20.0 | 8.344 | 50.377 | 20.082 | 2.121 | 15.836 | 3.240 | 38.039 | 53.1 | 172.3 | |
| 21.0 | 7.680 | 53.256 | 20.195 | 1.276 | 16.280 | 1.313 | 37.751 | 51.5 | 322.7 | propylene 3.9 l/h |
| 22.0 | 7.511 | 54.390 | 19.787 | 1.136 | 16.145 | 1.031 | 38.068 | 50.6 | 316.6 | |
| 23.5 | 7.678 | 54.717 | 19.654 | 1.077 | 16.027 | 0.847 | 36.758 | 50.2 | 314.3 | |
| 24.5 | 7.338 | 56.002 | 19.275 | 0.968 | 15.683 | 0.734 | 35.926 | 49.0 | 480.4 | propylene 6.1 l/h |
| 25.5 | 7.069 | 59.615 | 17.895 | 0.000 | 14.937 | 0.484 | 32.832 | 45.2 | 443.1 | |
| 26.5 | 6.978 | 60.337 | 17.542 | 0.000 | 14.704 | 0.439 | 32.246 | 44.5 | 435.8 | |
| 27.5 | 7.063 | 60.643 | 17.401 | 0.000 | 14.626 | 0.267 | 32.027 | 44.2 | 433.0 | |
| 28.5 | 7.078 | 60.635 | 17.707 | 0.000 | 14.611 | 0.269 | 32.018 | 44.2 | 432.9 | |
| 29.5 | 7.093 | 60.968 | 17.216 | 0.000 | 14.473 | 0.250 | 31.689 | 43.8 | 429.1 | |
| 30.5 | 7.179 | 60.829 | 17.298 | 0.000 | 14.501 | 0.193 | 31.799 | 44.0 | 430.5 | |
| 31.5 | 6.931 | 60.849 | 17.407 | 0.000 | 14.617 | 0.196 | 32.024 | 44.1 | 432.1 | |
| 32.5 | 6.793 | 61.454 | 17.088 | 0.000 | 14.422 | 0.243 | 31.510 | 43.5 | 425.9 | |
| 33.5 | 7.101 | 61.974 | 17.223 | 0.000 | 14.449 | 0.253 | 31.672 | 43.8 | 429.0 | |
| 34.5 | 7.171 | 61.716 | 17.371 | 0.000 | 14.572 | 0.270 | 31.943 | 44.1 | 432.1 | |
| 35.5 | 7.046 | 61.250 | 17.102 | 0.000 | 14.356 | 0.246 | 31.458 | 43.5 | 426.3 | |
| 36.5 | 6.947 | 61.015 | 17.293 | 0.000 | 14.545 | 0.200 | 31.838 | 43.9 | 430.1 | |
| 37.5 | 6.621 | 61.092 | 16.870 | 0.000 | 14.160 | 0.257 | 31.030 | 42.8 | 419.7 | |
| 38.5 | 6.692 | 61.793 | 17.033 | 0.000 | 14.297 | 0.185 | 31.330 | 43.2 | 423.1 | |
| 39.5 | 6.744 | 61.868 | 16.939 | 0.000 | 14.206 | 0.242 | 31.145 | 43.0 | 431.4 | |
| 40.5 | 6.512 | 62.036 | 16.972 | 0.000 | 14.229 | 0.251 | 31.201 | 43.0 | 431.2 | |
| 41.5 | 6.488 | 62.767 | 16.563 | 0.000 | 13.969 | 0.240 | 30.505 | 42.2 | 413.0 | |
| 42.5 | 6.416 | 62.807 | 16.596 | 0.000 | 13.222 | 0.959 | 29.818 | 41.6 | 407.4 | |
| 43.5 | 6.423 | 63.292 | 16.263 | 0.000 | 13.795 | 0.227 | 30.058 | 41.6 | 407.5 | |

The tungsten content of an unused catalyst was 2.1% and after the reaction 2.5%.

EXAMPLE 8

The sample was dimesitylene bis(cyclohexane diolato) tungsten.

0.29 g of the sample and 0.94 g of silica were impregnated. 0.5425 g of the catalyst was packed in the reactor and a calcination was performed with nitrogen (ca. 10 l/h, 600° C., 1 h). A brown greenish oil was observed during the calcination. It was allowed to react with propene, and test results showing the activity of the metathesis catalyst are shown in Table 3.

TABLE 3

ACTIVITY OF A METATHESIS CATALYST

| | |
|---|---|
| No. of run: | L3 |
| Date: | Mar 29–30, 1990 |
| PRECURSOR: | Dimesitylene bis(cyclohexane diolato)tungsten |
| Carrier: | SiO2 PQ cs-1231 0.6–1.6 mm |
| Mass of catalyst (g): | 0.5425 |
| Area of catalyst (m$^2$/g) | 310 |
| Molar mass of metal (g/mol): | 183.85 |
| Content of metal (%): | 1.4 |
| Temperature (°C.): | 400 |
| Activation: | N2 ca. 10 l/h 600° C. 1 h |
| Propylene flow (l/h): | 1–6 |

| Time (h) | Ethylene (%) | Propylene (%) | Trans-2-butene (%) | 1-butene (%) | Cis-2-butene (%) | Others (%) | Butenes (%) | Propylene conversion (%) | Activity (g/gh) | Notes |
|---|---|---|---|---|---|---|---|---|---|---|
| 0.0 | 12.598 | 49.667 | 17.446 | 3.150 | 12.732 | 4.407 | 33.328 | 50.2 | 91.3 | propylene 1.0 l/h |
| 1.0 | 6.436 | 58.076 | 18.076 | 0.000 | 15.182 | 2.230 | 33.258 | 46.2 | 336.6 | propylene 4.0 l/h |
| 2.5 | 10.345 | 56.415 | 18.114 | 0.368 | 14.361 | 0.397 | 32.843 | 46.6 | 339.5 | |
| 3.5 | 7.526 | 53.699 | 21.545 | 0.000 | 16.867 | 0.363 | 38.412 | 51.8 | 377.0 | |
| 19.0 | 10.712 | 53.494 | 19.494 | 0.516 | 15.124 | 0.540 | 35.134 | 49.6 | 361.1 | |

TABLE 3-continued

| | | | ACTIVITY OF A METATHESIS CATALYST | | | | | | | |
|---|---|---|---|---|---|---|---|---|---|---|
| 20.0 | 10.041 | 56.116 | 18.476 | 0.415 | 14.531 | 0.421 | 33.422 | 47.2 | 343.7 | |
| 20.5 | 7.759 | 53.112 | 21.451 | 0.000 | 17.001 | 0.677 | 38.452 | 52.1 | 379.2 | |
| 21.5 | 6.335 | 55.258 | 21.064 | 0.000 | 16.707 | 0.636 | 37.771 | 50.6 | 368.7 | |
| 22.5 | 5.283 | 62.775 | 17.421 | 0.000 | 14.371 | 0.150 | 31.792 | 43.2 | 471.7 | propylene 6.0 l/h |
| 23.5 | 6.543 | 60.468 | 18.108 | 0.000 | 14.678 | 0.203 | 32.786 | 44.9 | 490.0 | |
| 24.0 | 9.026 | 62.826 | 15.344 | 0.000 | 12.627 | 0.117 | 27.971 | 40.0 | 437.5 | |
| 25.0 | 6.449 | 60.353 | 18.183 | 0.000 | 14.825 | 0.190 | 33.008 | 45.1 | 492.4 | |
| 26.0 | 6.273 | 61.226 | 17.784 | 0.000 | 14.542 | 0.175 | 32.326 | 44.2 | 482.9 | |

The tungsten content of an unused catalyst was 1.4% and the corresponding percentage after the reaction was 1.9%.

REFERENCE EXAMPLES 9-10

Two reference catalyst were prepared and tested. One of the catalysts was tungsten oxide chloride $WOCl_4$, which is a tungsten complex dissolving in non-polar solvents, and the other one on a water-soluble salt $(NH_4)_2WO_4$, which is the most common reactant in metathesis catalysts.

EXAMPLE 9

A reference catalyst from $WOCl_4$, a low tungsten content.

0.18 g of tungsten oxychloride was added gradually to and by simultaneously mixing with 1.28 g. of silica in dichloromethane (0.6–1.6 mm, 310 m²/g, The PQ Corporation). They were allowed to absorb at room temperature for about 3 hours, after which they were evaporated in a vacuum. The tungsten content was determined to be 2.3%.

0.5302 g of the catalyst was loaded into a reactor tube, calcinated with air at 600° C. and flushed with nitrogen. It was tested in a metathesis reaction of propene at flows 1.0–6.0 l/h. The tungsten content after the run was 2.2%.

TABLE 4

| ACTIVITY OF A METATHESIS CATALYST Micro 1 | |
|---|---|
| Code of run: | WOCl4 |
| Date: | Apr 18–20, 1990 |
| PRECURSOR: | W(O)Cl4 |
| Carrier: | SiO2 PQ cs-1231 0.6–1.6 mm |
| Mass of catalyst before run (g): | 0.5302 |
| after run (g) | 0.3014 |
| Content of metal before run (%): | 2.3 |
| after run (%): | 2.2 |
| Activation: | air ca 10 l/h 600° C. |
| | 2 h W2 ca. 10 l/h |
| | 400° C. 1.5 h |
| Temperature (°C.) | 400 |
| Propylene flow (l/h): | 1–6 |

| Time (h) | Ethylene (%) | Propylene (%) | Trans-2-butene (%) | 1-butene (%) | Cis-2-butene (%) | Others (%) | Butenes (%) | Propylene conversion (%) | Activity (g/gh) | Notes |
|---|---|---|---|---|---|---|---|---|---|---|
| 1.0 | 3.196 | 86.581 | 4.883 | 0.590 | 4.674 | 10.147 | 0.076 | 15.0 | 31.2 | propylene 1.0 l/h |
| 2.0 | 3.086 | 78.327 | 7.352 | 0.659 | 3.451 | 11.462 | 7.125 | 18.0 | 37.5 | |
| 3.0 | 4.627 | 77.705 | 8.788 | 0.736 | 8.504 | 18.028 | 0.000 | 25.8 | 53.8 | |
| 4.0 | 4.323 | 75.581 | 9.936 | 0.816 | 9.344 | 20.096 | 0.000 | 28.5 | 59.5 | |
| 5.0 | 4.313 | 74.458 | 10.519 | 0.721 | 9.989 | 21.229 | 0.000 | 30.0 | 62.5 | |
| 6.0 | 4.471 | 73.174 | 10.975 | 0.714 | 10.396 | 22.085 | 0.000 | 31.2 | 65.0 | |
| 7.0 | 4.900 | 72.095 | 11.523 | 0.796 | 10.687 | 23.006 | 0.000 | 32.4 | 67.5 | |
| 8.0 | 5.082 | 71.506 | 11.694 | 0.673 | 11.046 | 23.413 | 0.000 | 32.9 | 68.7 | |
| 9.0 | 5.151 | 70.984 | 11.931 | 0.648 | 11.286 | 23.865 | 0.000 | 33.5 | 69.9 | |
| 10.0 | 5.234 | 70.247 | 12.292 | 0.632 | 11.595 | 24.519 | 0.000 | 34.4 | 71.7 | |
| 11.0 | 5.391 | 69.997 | 12.379 | 0.608 | 11.625 | 24.612 | 0.000 | 34.5 | 72.0 | |
| 12.0 | 5.683 | 69.477 | 12.505 | 0.598 | 11.737 | 24.840 | 0.000 | 34.9 | 72.8 | |
| 13.0 | 5.633 | 68.700 | 12.998 | 0.715 | 11.954 | 25.667 | 0.000 | 35.9 | 74.9 | |
| 14.0 | 5.794 | 68.688 | 12.884 | 0.576 | 12.058 | 25.518 | 0.000 | 35.8 | 74.6 | |
| 15.5 | 5.652 | 68.269 | 13.270 | 0.694 | 11.115 | 26.079 | 0.000 | 36.4 | 76.0 | |
| 16.5 | 6.011 | 68.169 | 13.069 | 0.559 | 12.192 | 25.820 | 0.000 | 36.2 | 75.6 | |
| 17.5 | 5.969 | 67.759 | 13.371 | 0.655 | 12.246 | 26.272 | 0.000 | 36.8 | 76.7 | |
| 18.5 | 5.981 | 67.889 | 13.241 | 0.543 | 12.345 | 26.129 | 0.000 | 36.6 | 76.3 | |
| 19.5 | 5.947 | 67.879 | 13.298 | 0.527 | 12.349 | 26.174 | 0.000 | 36.6 | 76.4 | |
| 20.5 | 2.472 | 85.064 | 6.129 | 0.000 | 6.334 | 12.463 | 0.000 | 18.0 | 150.3 | propylene 4.0 l/h |
| 21.5 | 2.610 | 85.665 | 6.212 | 0.000 | 6.514 | 12.726 | 0.000 | 18.4 | 153.5 | |
| 22.5 | 2.792 | 84.778 | 6.076 | 0.000 | 6.354 | 12.430 | 0.000 | 18.0 | 150.4 | |
| 23.5 | 2.757 | 84.937 | 6.073 | 0.000 | 6.233 | 12.306 | 0.000 | 17.9 | 148.9 | |
| 24.5 | 1.941 | 87.884 | 4.923 | 0.000 | 5.252 | 10.175 | 0.000 | 14.8 | 185.2 | propylene 6.0 l/h |
| 25.5 | 2.068 | 87.968 | 4.836 | 0.000 | 5.129 | 9.965 | 0.000 | 14.5 | 181.8 | |
| 26.5 | 2.044 | 88.475 | 4.592 | 0.000 | 4.889 | 9.481 | 0.000 | 13.8 | 173.3 | |
| 27.5 | 4.639 | 74.452 | 10.445 | 0.513 | 9.952 | 20.910 | 0.000 | 29.6 | 61.8 | propylene 1.0 l/h |

TABLE 4-continued

ACTIVITY OF A METATHESIS CATALYST Micro 1

| | | | | | | | | | |
|---|---|---|---|---|---|---|---|---|---|
| 28.5 | 5.275 | 71.696 | 11.784 | 0.000 | 11.244 | 23.028 | 0.000 | 32.5 | 67.8 |
| 29.5 | 5.573 | 70.538 | 12.366 | 0.000 | 11.522 | 23.888 | 0.000 | 33.7 | 70.3 |
| 30.5 | 5.796 | 70.116 | 12.388 | 0.000 | 11.700 | 24.088 | 0.000 | 34.0 | 70.9 |
| 31.5 | 5.737 | 69.872 | 12.525 | 0.000 | 11.865 | 24.390 | 0.000 | 34.4 | 71.7 |
| 32.5 | 5.755 | 69.650 | 12.631 | 0.000 | 11.964 | 24.595 | 0.000 | 34.6 | 72.2 |
| 33.5 | 5.751 | 69.383 | 12.891 | 0.000 | 11.975 | 24.866 | 0.000 | 35.0 | 72.9 |
| 34.5 | 5.839 | 69.325 | 12.746 | 0.000 | 12.090 | 24.836 | 0.000 | 35.0 | 72.9 |
| 35.5 | 5.783 | 69.297 | 12.809 | 0.000 | 12.111 | 24.920 | 0.000 | 35.0 | 73.1 |
| 36.5 | 5.626 | 69.041 | 13.014 | 0.000 | 12.319 | 25.333 | 0.000 | 35.5 | 74.0 |
| 37.5 | 6.069 | 68.330 | 13.304 | 0.000 | 12.297 | 25.601 | 0.000 | 36.0 | 75.0 |
| 38.5 | 5.885 | 68.303 | 13.408 | 0.000 | 12.404 | 25.812 | 0.000 | 36.2 | 75.5 |
| 39.5 | 6.112 | 68.219 | 13.220 | 0.000 | 12.448 | 25.668 | 0.000 | 36.1 | 75.2 |
| 40.5 | 6.020 | 68.177 | 13.407 | 0.000 | 12.396 | 25.903 | 0.000 | 36.2 | 75.5 |
| 41.5 | 6.025 | 68.316 | 13.263 | 0.000 | 12.423 | 25.686 | 0.000 | 36.1 | 75.2 |
| 42.5 | 5.921 | 68.312 | 13.287 | 0.000 | 12.480 | 25.767 | 0.000 | 36.1 | 75.4 |

EXAMPLE 10

A reference catalyst from $(NH_4)_2WO_4$, normal tungsten content.

A 3.9% water solution of ammonium tungstate 35.30 g was added gradually to and by simultaneously mixing with 19.96 g of silica (0.6–1.6 mm, 310 m²/g, The PQ Corporation). They were allowed to absorb at 80° C. for about one hour, after which they were evaporated at 115° C. for 17 hours.

16.7 g of the same solution was impregnated once again, it was allowed to absorb at 80° C. and dried at 115° C. for 23 hours. The metallic content was determined to be 5.8%.

0.3782 g of the catalyst was loaded into a reactor tube, calcinated with air at 600° C. and flushed with nitrogen. It was tested in a metathesis reaction of propene at flows 0.1–4.1 l/h. The tungsten content after the run was 6.3%.

The test results of the activity of the metathesis catalyst are shown in Table 5.

TABLE 5

ACTIVITY OF A METATHESIS CATALYST

| | |
|---|---|
| No. of run: | Test 15 |
| Date: | Jul 31–Aug 3, 1989 |
| PRECURSOR: | (NH4)2WO4 |
| Carrier: | Silica PQ cs-1231 0.6–1.6 mm |
| Mass of unused catalyst (g): | 0.3782 |
| Mass of catalyst used (g): | 0.3664 |
| Metal content before run (%): | 5.8 |
| Metal content after run (%): | 6.3 |
| Activation: | air ca. 10 l/H 600° C. 1.5 h, N2 10 l/h 600° C. 0.5 h |
| Temperature (°C.): | 400 |
| Propylene flow (l/h): | 0.9–4.09 |

| Time (h) | Ethylene (%) | Propylene (%) | Trans-2-butene (%) | 1-butene (%) | Cis-2-butene (%) | Others (%) | Butenes (%) | Propylene conversion (%) | Activity (g/gh) | Notes |
|---|---|---|---|---|---|---|---|---|---|---|
| 1.01 | 4.378 | 76.505 | 6.668 | 1.891 | 5.505 | 5.503 | 14.064 | 21.6 | 14.2 | 400° C. 1.1 l/h |
| 2.0 | 6.111 | 73.233 | 9.204 | 2.322 | 7.628 | 1.502 | 19.154 | 28.2 | 18.6 | |
| 4.0 | 7.635 | 66.508 | 11.827 | 2.563 | 9.650 | 1.817 | 25.040 | 35.2 | 23.2 | |
| 7.0 | 8.939 | 61.344 | 13.676 | 3.210 | 10.795 | 2.036 | 27.681 | 40.4 | 26.6 | |
| 8.0 | 9.015 | 61.178 | 13.850 | 3.004 | 10.910 | 2.043 | 27.764 | 40.5 | 26.7 | |
| 11.0 | 9.151 | 60.485 | 14.429 | 2.686 | 11.417 | 1.832 | 28.532 | 41.4 | 27.3 | |
| 12.0 | 9.034 | 60.840 | 14.450 | 2.389 | 11.498 | 1.789 | 28.337 | 41.1 | 27.1 | |
| 16.0 | 9.361 | 59.583 | 15.055 | 2.339 | 11.879 | 1.783 | 29.273 | 42.4 | 28.0 | |
| 17.0 | 9.334 | 59.596 | 15.081 | 2.302 | 11.922 | 1.765 | 29.305 | 42.4 | 28.0 | |
| 18.0 | 9.529 | 59.902 | 15.304 | 2.499 | 11.959 | 1.807 | 29.762 | 43.1 | 28.4 | |
| 19.0 | 9.455 | 59.027 | 15.305 | 2.351 | 12.058 | 1.804 | 29.714 | 43.0 | 28.4 | |
| 20.0 | 9.412 | 59.227 | 15.297 | 2.321 | 12.044 | 1.699 | 29.622 | 42.9 | 28.3 | |
| 21.0 | 9.535 | 59.134 | 15.672 | 2.176 | 12.290 | 1.193 | 30.138 | 43.3 | 28.6 | |
| 22.0 | 11.956 | 59.594 | 15.110 | 3.487 | 10.751 | 2.102 | 29.348 | 44.8 | 13.6 | 400° C. 0.52 l/h |
| 23.0 | 12.006 | 56.245 | 14.814 | 3.896 | 10.524 | 2.515 | 29.234 | 43.8 | 13.6 | |
| 24.0 | 11.970 | 56.583 | 14.565 | 3.956 | 10.375 | 2.551 | 28.896 | 43.4 | 13.5 | |
| 27.5 | 12.574 | 57.121 | 13.803 | 4.160 | 9.797 | 2.545 | 27.760 | 42.2 | 13.1 | |
| 28.5 | 9.341 | 59.644 | 14.912 | 2.526 | 11.846 | 1.731 | 29.284 | 42.4 | 28.0 | 400° C. 1.1 l/h |

As shown in Tables 2–5, in the product distribution, the ratio between ethene and butenes, the molar ratio is not 1:1 which is required by theory (the ratio of the weight percentages was ca. 1:2), since some ethene disappears from the system before the analysis. The conversion and the activity have been calculated from the butene observed.

While the invention has been described with respect to the production of particular catalysts and the use thereof in particular metathesis reactions of olefines, it is to be understood that variations and modifications of the invention can be made. Such modifications are meant to be comprehended within the meaning and scope of the claims herein.

What is claimed is:

1. Catalyst for metathesis reactions of olefines, said catalyst comprising a tungsten precursor complex with the structure $W(ArCH_2)_2(diol)_2$, wherein $ArCH_2$ is benzene substituted with a lower alkyl group and said diol is 1,2-cyclohexane diol or pinacol, said tungsten precursor complex being impregnated in an inorganic carrier and calcinated.

2. The catalyst of claim 1, wherein the substituted benzene is mesitylene.

3. The catalyst of claim 1, wherein $ArCh_2$ is mesitylene and said complex is impregnated in silica.

4. The catalyst of claim 2, wherein said complex is impregnated in silica.

5. The catalyst according to claim 1, wherein said complex is impregnated in silica and calcinated.

6. A method for preparing a heterogenous catalyst for the metathesis reaction of olefines, which comprises;
   a) forming a complex between an inorganic tungsten salt and a diol,
   b) reacting the thus obtained complex with a benzyl anion or a benzyl anion substituted with a lower alkyl group, thus obtaining a tungsten complex containing diol ligands and benzyl ligands or benzyl ligands substituted with a lower alkyl group, and
   c) impregnating the thus obtained tungsten complex into a carrier and calcinating.

7. The method according to claim 6, wherein the inorganic tungsten salt is a tungsten halogenide.

8. The method of claim 6, wherein the inorganic tungsten salt is $WCl_6$.

9. The method according to claim 6, wherein the diol is picanol or 1,2-cyclohexane diol.

10. The method according to claim 8, wherein the diol is picanol or 1,2-cyclohexane diol.

11. The method according to claim 6, wherein the carrier is a silica.

12. The method according to claim 6, wherein the complex of the tungsten salt and the diol is treated with a halogenide of a benzene substituted with a lower alkyl group, preferably with a bromide and a magnesium metal.

13. The method according to claim 6, wherein the complex of the tungsten salt and the diol is treated with a bromide of a benzene substituted with a lower alkyl group, and with magnesium metal.

14. The method according to claim 6, wherein the impregnation is effected from an inert solvent into a carrier.

15. The method according to claim 14, wherein said carrier is a silica.

16. The method according to claim 6, wherein the calcination is effected with an inert gas at a temperature of about 400°–800° C.

17. The method according to claim 16, wherein said inert gas is nitrogen.

* * * * *